United States Patent
Brugnoli et al.

(10) Patent No.: US 8,062,002 B2
(45) Date of Patent: Nov. 22, 2011

(54) VACUUM UNIT FOR STEAM STERILIZER

(75) Inventors: Adam L. Brugnoli, Pennsburg, PA (US); Kenneth G. Brownlow, III, Morgantown, PA (US); Phillip B. DeMarra, Narvon, PA (US); Todd A. Becker, Sinking Springs, PA (US); Daniel Gonzalez, East Earl, PA (US); Andrew J. Dillow, Honey Brook, PA (US); Alan C. Cinquegrana, Brick, NJ (US)

(73) Assignee: R-V Industries, Inc, Honey Brook, PA (US)

(*) Notice: Subject to any disclaimer, the term of this patent is extended or adjusted under 35 U.S.C. 154(b) by 789 days.

(21) Appl. No.: 12/126,052

(22) Filed: May 23, 2008

(65) Prior Publication Data

US 2009/0288721 A1 Nov. 26, 2009

(51) Int. Cl.
*F04B 23/08* (2006.01)
*A61L 2/00* (2006.01)
*A61L 9/00* (2006.01)
(52) U.S. Cl. .............................. 417/88; 422/26; 422/292
(58) Field of Classification Search ................ 417/76, 417/77, 87, 88, 80, 187; 34/77, 92; 237/67; 422/26, 292; 137/565.22
See application file for complete search history.

(56) References Cited

U.S. PATENT DOCUMENTS

| | | | | |
|---|---|---|---|---|
| 1,438,008 A | * | 12/1922 | Young | 417/80 |
| 5,000,907 A | * | 3/1991 | Chevereau et al. | 376/282 |
| 5,906,800 A | * | 5/1999 | Napierkowski et al. | 422/298 |
| 5,997,813 A | * | 12/1999 | Yaskoff et al. | 422/26 |

OTHER PUBLICATIONS

Drawing No. D-82-16118, May 22, 2006.
Drawing No. D-82-17326, Jul. 10, 2006.

* cited by examiner

*Primary Examiner* — Devon C Kramer
*Assistant Examiner* — Bryan Lettman
(74) *Attorney, Agent, or Firm* — Howson & Howson LLP

(57) ABSTRACT

In a vacuum unit for use in drawing a vacuum on a steam sterilizer, a pump circulates water through an ejector and a reservoir. Fresh water is injected at the pump inlet to maintain a low temperature in the ejector so that it can operate efficiently. Excess water is taken from a location adjacent the bottom of the reservoir through an internal dip tube, and passed through a U-shaped conduit that serves as a condensate trap. To maintain the water discharge temperature below a predetermined level, fresh water is injected into the U-shaped conduit through a valve controlled by a temperature sensor downstream from the water injection point.

9 Claims, 4 Drawing Sheets

VACUUM UNIT FOR STEAM STERILIZER

FIELD OF THE INVENTION

This invention relates to vacuum systems, and particularly to improvements for reducing water consumption in the operation of vacuum systems used to withdraw air and condensate from steam sterilizers.

BACKGROUND OF THE INVENTION

Steam sterilizers, also referred to as "autoclaves," are widely used in a variety of applications for eliminating contaminating microorganisms from articles such as surgical instruments and other hospital equipment, laboratory equipment, and pharmaceutical and medical products.

In the operation of a steam sterilizer, after charging the sterilizer chamber with articles to be sterilized, air is drawn out of the chamber by applying a vacuum. Drawing of the vacuum is discontinued, and steam is then injected into the chamber. After the articles in the chamber have been exposed to steam for a sufficient time, drawing the vacuum can be resumed to remove steam, water vapor and condensate. In some cases, the cycle consisting of drawing the vacuum and injecting steam can be repeated while sterilizing a particular set of articles.

The vacuum is conventionally produced by using a pump to pump water through an ejector (also known as an "eductor"), a device comprising a narrowed passage, i.e., a venturi, for increasing the velocity of flow and thereby producing a vacuum. The water is typically circulated through the ejector through a path that includes a reservoir.

An ejector operates more efficiently at lower temperatures. For example, with a typical ejector, in order to reach a vacuum level of 700 mm of Mercury within five minutes, a water temperature of 29° C. is typically required. However, when an ejector is used to draw a vacuum on a steam sterilizer, steam, hot water vapor and hot condensate are introduced into the circulating water, increasing its temperature. Therefore, to maintain efficient operation of the ejector, cool water is added to the reservoir.

Because condensate and cooling water are added to the recirculating water stream, the total volume of water in the system continually increases, and it is necessary to discharge water to a drain. Plumbing codes typically require the effluent discharged by sterilizing equipment to a water drain to be at a temperature not greater than 140° F. (60° C.). Thus it is also necessary to add cooling water in order to bring the temperature of the effluent down to the required level. Large quantities of cooling water are required to achieve efficient ejector operation and to satisfy effluent temperature requirements. However, the significant water requirements of vacuum equipment associated with steam sterilizers have caused environmental concerns, especially in arid geographic areas.

BRIEF SUMMARY OF THE INVENTION

This invention addresses the problem of excessive water usage in a vacuum unit associated with steam sterilization equipment.

A vacuum unit in accordance with the invention comprises, as its principal elements, an ejector, a pump, a reservoir, and first and second water control valves. The ejector has an ejector passage for flow of water from an ejector inlet to an ejector outlet, and a steam inlet connectable to the chamber drain of a steam sterilizer. The steam inlet of the ejector is connected to the ejector passage, and the ejector passage has a restriction for generating a vacuum at the steam inlet when water flows through the ejector passage from the ejector inlet to the ejector outlet. The reservoir has a first reservoir outlet and a reservoir inlet. The pump has a pump inlet connected to the first reservoir outlet and a pump outlet connected to the ejector inlet. The pump produces a flow of water through the ejector passage. An ejector outlet conduit connects the ejector outlet to the reservoir inlet.

A drain conduit is connectable from the second reservoir outlet to a drain. The unit also includes a water supply conduit connectable to a source of water. A first water supply passage is connected from the water conduit to the pump inlet, and a first valve control flow of water through the first water supply passage. A second water supply passage, connected from the water supply conduit to the second reservoir conduit, introduces water from a source of water into the drain conduit. A second valve controls flow of water through the second water supply passage.

In a preferred embodiment of the invention, the reservoir inlet comprises a perforated tube having perforations, and connected to the ejector outlet conduit, for dispersing fluid drawn from the steam inlet into the reservoir.

In the preferred embodiment, the second water supply passage is connected, by a direct connection, to the drain conduit, a temperature sensor is located in the drain conduit, downstream from said direct connection, and the second valve is a sensor-responsive valve, connected and responsive, to the temperature sensor.

The drain conduit preferably includes a U-shaped trap, which comprises a first upright section connected to the second reservoir outlet, a second upright section having a drain outlet, and a connecting section connecting lower ends of the first and second upright sections. The second water supply passage is connected, by a direct connection, to the second upright section of the U-shaped trap. Preferably, a temperature sensor is located in the second upright section downstream from said direct connection, and the second valve is a sensor-responsive valve, connected, and responsive, to the temperature sensor.

In accordance with another aspect of the invention, the second reservoir outlet may include an upright tube located within the reservoir. The upright tube has an inlet opening adjacent the bottom of the reservoir, an outlet connection adjacent the top of the reservoir, and an opening inside the reservoir adjacent the top of the reservoir.

By incorporation of the above-mentioned features, the vacuum unit in accordance with the invention can achieve a high level of vacuum suitable for operation of a steam sterilizer, rapidly, efficiently, and with a greatly reduced rate of water consumption.

Other objects, details and advantages of the invention will be apparent from the following detailed description when read in conjunction with the drawings.

DETAILED DESCRIPTION OF THE PREFERRED EMBODIMENT

Figure 1:
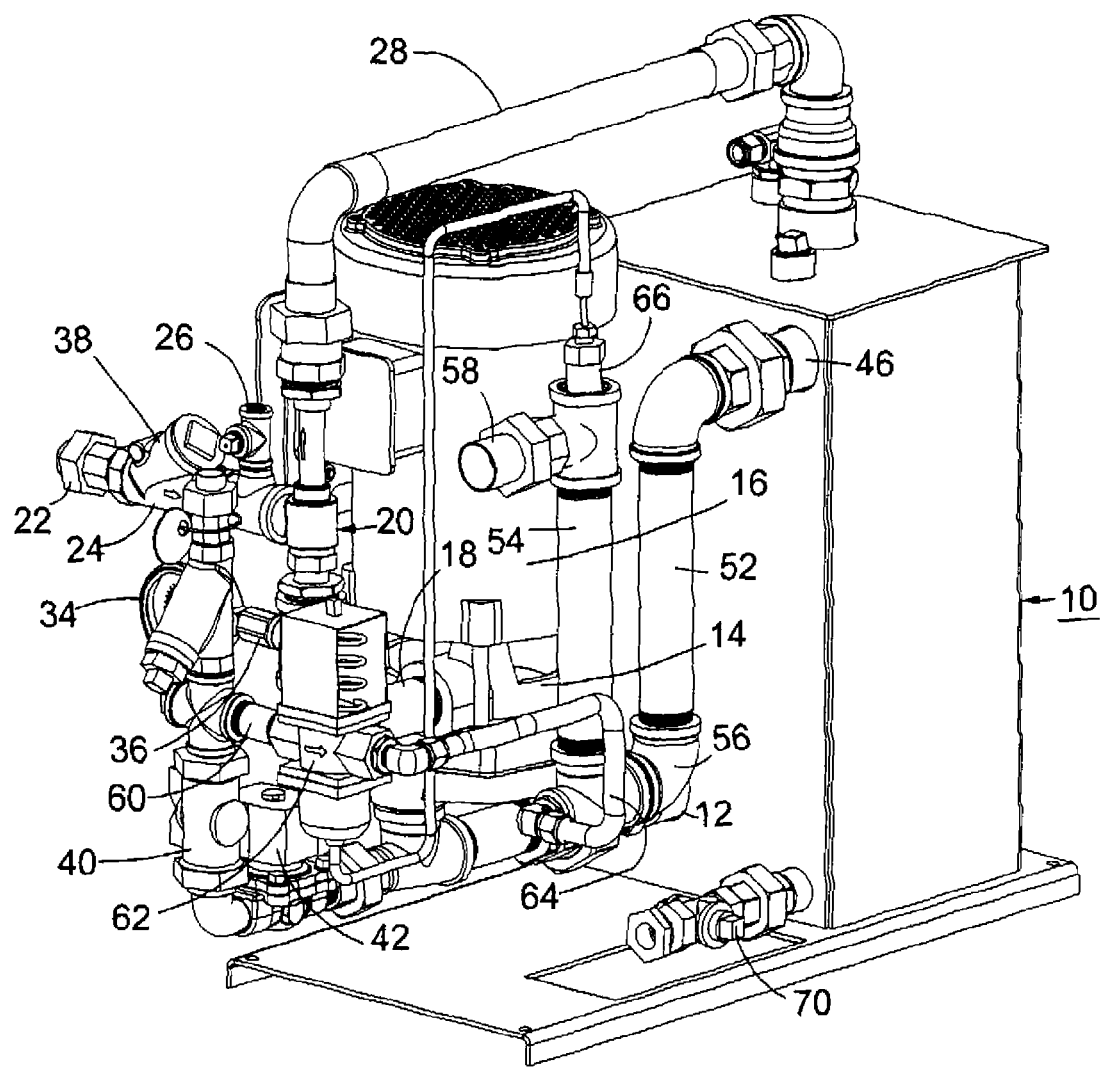
FIG. 1 is an oblique perspective view of a vacuum unit in accordance with the invention.
Figure 2:
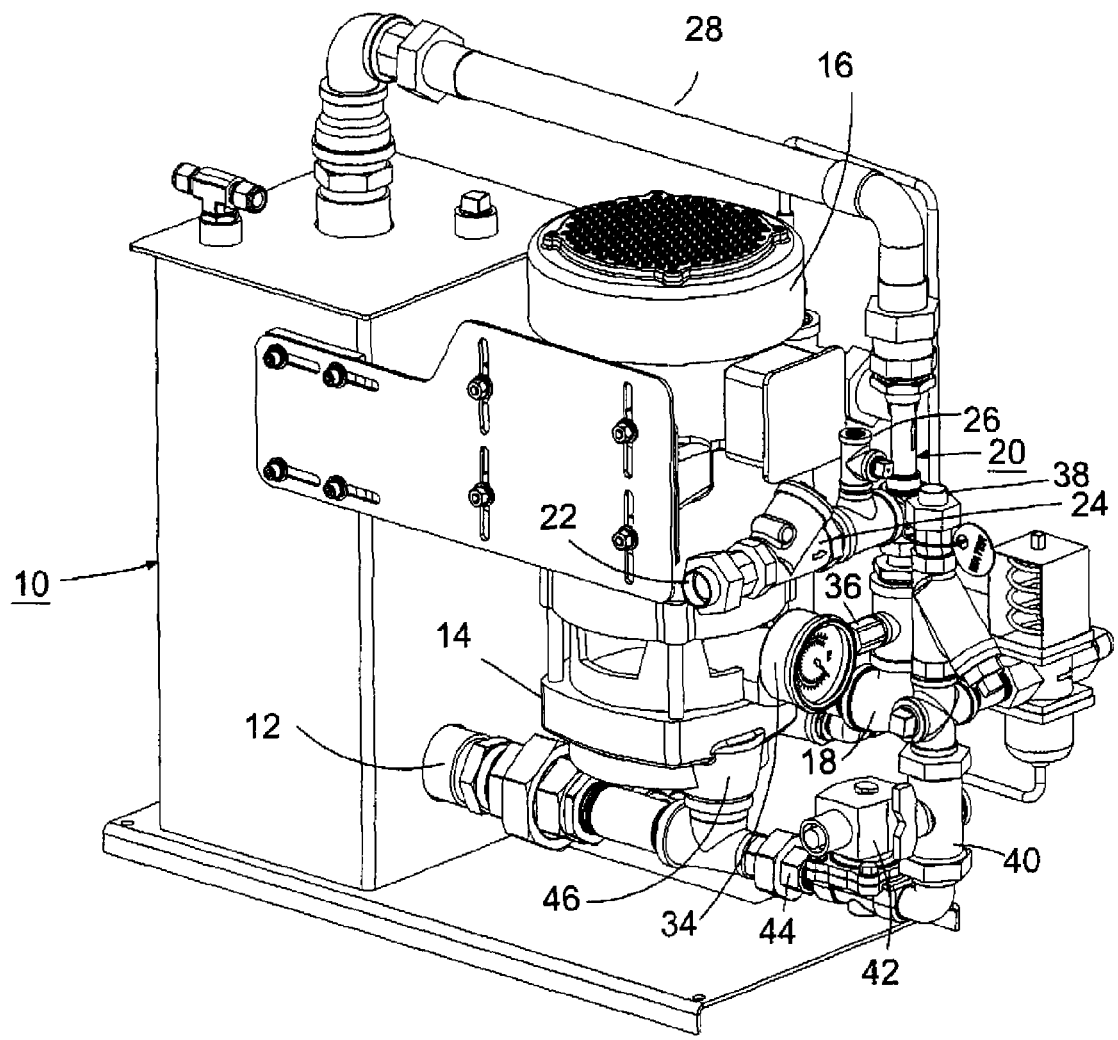
FIG. 2 is an oblique perspective view, showing the opposite side of the vacuum unit in FIG. 1.
Figure 3:
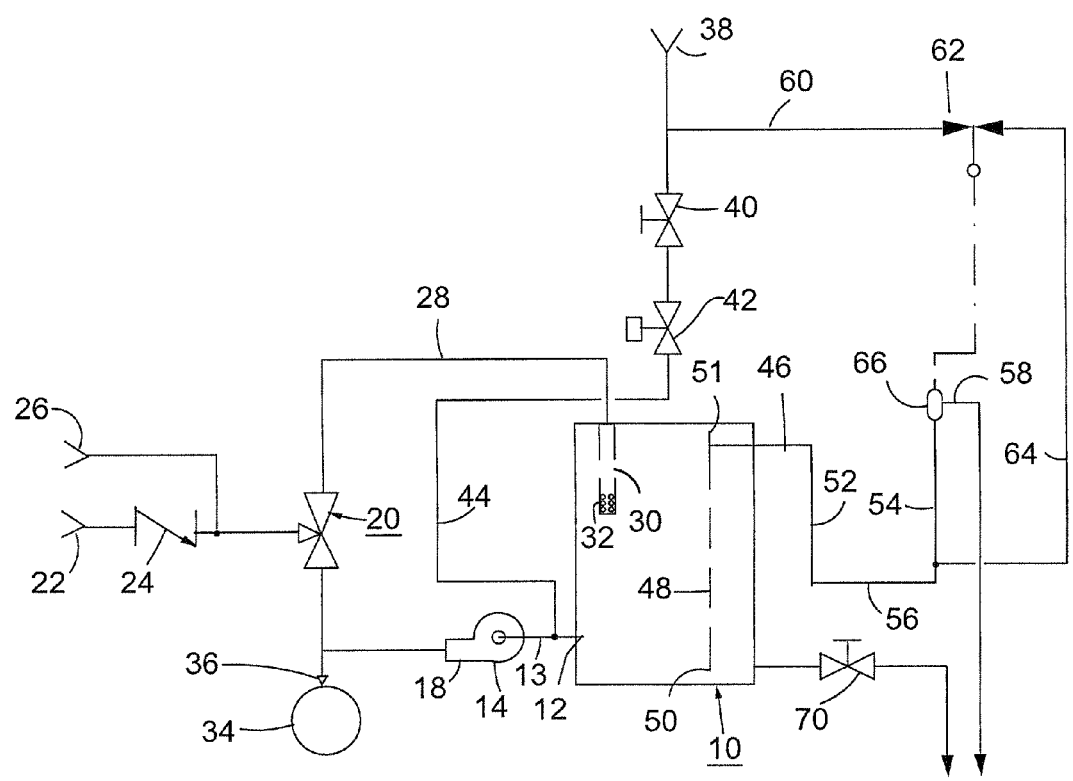
FIG. 3 is a schematic diagram of the vacuum unit.

As shown in FIGS. 1-3, the vacuum unit comprises a tank 10, which serves as a water reservoir. Water is drawn from the tank, through a tank outlet 12 and a conduit 13, by a pump 14 driven by an electric motor 16. The outlet 18 of the pump leads to an ejector assembly 20, which comprises a restricted passage. The flow of water through the restricted passage produces a pressure drop, drawing a vacuum in pipe 22, which is connectable to the vacuum chamber of a steam sterilizer (not shown). Pipe 22 includes a check valve 24. Another inlet 26 is provided between the check valve and the ejector for drawing a vacuum for opening pressure-operated door seals in the sterilizer.

Water exiting the ejector is returned to the tank 10 through a pipe 28. Thus, a closed circuit is provided for circulation of water from the tank, through the pump and ejector, and back to the tank.

Because the ejector draws air, steam and water vapor from the sterilizer, the fluid exiting the ejector will contain air at times, and at other times, hot condensate from the sterilizer. The fluid is returned to the tank through a dispersion tube 30, shown in FIG. 4, the lower portion of which is provided with perforations 32. The total cross-sectional area of the perforations should be at least as great as the transverse cross-sectional area of the pipe 28. The perforations disperse fluid evenly into the tank 10 at a level below the surface of the water in the tank, thereby achieving improved cooling, while maintaining good recirculating flow through the ejector by virtue of the large total cross-sectional area of the perforations.

Pressure at the outlet of the pump 18 is monitored by a pressure gauge 34, which is preferably provided with a snubber 36 for absorbing shock in the line leading from the outlet of the pump to the ejector.

Fresh water, received through a fresh water inlet 38 is delivered though a pair of valves 40 and 42, connected in series, through line 44 directly to conduit 13, and through conduit 13 to the inlet of pump 14. Valve 40 is a manually operated, flow-restricting, needle valve, and valve 42 is a solenoid-operated valve that automatically opens when the pump 14 is in operation, and closes when the pump is not in operation.

The replenishment of water by injecting fresh water at the pump inlet instead of directly into the reservoir improves the efficiency of the ejector by maintaining a low temperature at the ejector inlet. This in turn reduces the amount of fresh water required, and makes it possible to achieve a greater vacuum and to achieve a desired vacuum within a shorter time.

As water is added to tank 10 through pipe 28 and perforated dispersion tube 30, water is forced out of the tank through outlet 46. As seen in FIG. 3, outlet 46 is connected to a dip tube 48 inside the tank. The dip tube has an inlet opening 50 adjacent the bottom of the tank, and also has an opening 51 at its upper end to allow for an air gap to prevent siphoning of the water from the tank.

The outlet 46 is connected to a U-shaped pipe comprising vertical sections 52 and 54, connected at their lower ends by a connecting pipe 56. A drain outlet 58 is provided at the upper end of pipe section 54.

Fresh water from inlet 38 is also delivered through pipe 60, a temperature control valve 62, and pipe 64 to the U-shaped pipe at a location near the lower end of vertical section 54. Valve 62 is controlled by a sensor 66 at the upper end of vertical pipe section 54.

The configuration of piping and controls at the outlet of reservoir maintains the discharge temperature below the prescribed maximum temperature (60° C.), and minimizes use of fresh water for quenching. In particular, because the water at the bottom of tank 10 is cooler than the water closer to the top of the tank, the use of the dip tube 48 causes cooler water to be delivered through the outlet 46. Secondly, by locating the sensor 66 of temperature control valve 62 downstream from the location at which fresh water from valve 62 is injected into the discharge stream from pipe 64, a greater cooling efficiency is achieved. Moreover, the location of the sensor downstream from the fresh water injection point provides positive assurance that the discharge temperature is below 60° C. Third, the U-shaped pipe connected to outlet 46 traps condensate, thereby improving the cooling effect of the injected fresh water on the discharge stream.

A normally closed tank drain valve 70 is provided adjacent the bottom of the tank 10.

The vacuum unit according to the invention exhibits environmentally important advantages in that it enables a steam sterilizer to be operated efficiently, and to reach a desired vacuum level in a shorter time, with a significant reduction in the amount of water consumed in the operation of the vacuum system, and without the need for refrigeration of the water supply.

Figure 4:
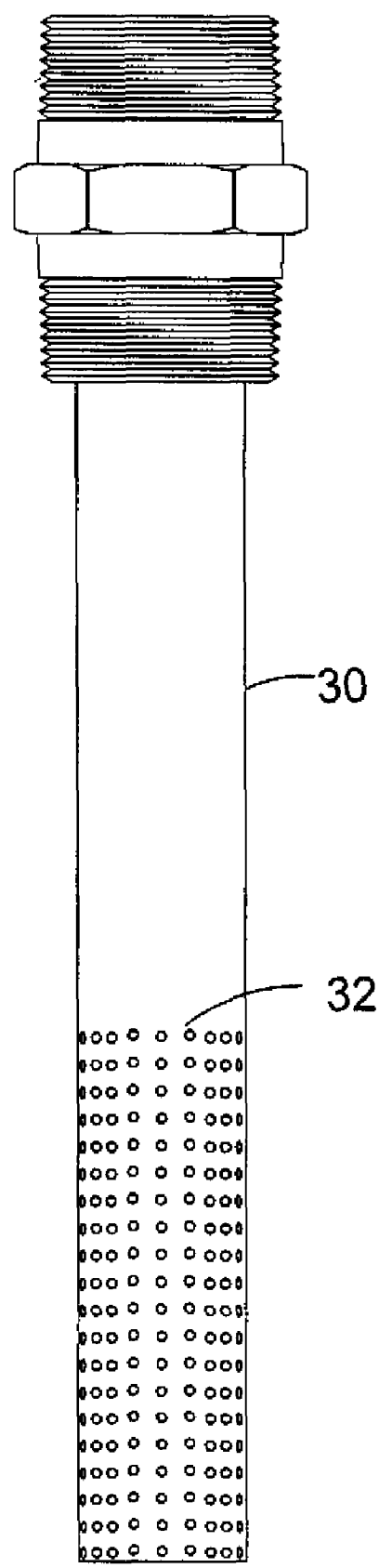
FIG. 4 is an elevational view of a perforated dispersing tube.

Various modifications can be made to the apparatus described. For example, water can be returned from the ejector to the reservoir tank through a perforated plate or other suitable perforated structure rather than through a perforated tube as shown in FIG. 4. Valve 42 can be equipped with an electronic control whereby the opening and closing of the valve is based on comparison of a preset vacuum level and a current measured vacuum level, and the system can be software controlled. Still other modifications may be made to the apparatus and method described above without departing from the scope of the invention as defined in the following claims.

What is claimed is:

1. A vacuum unit for use with a steam sterilizer comprising:
    an ejector having an ejector passage for a flow of water from an ejector inlet to an ejector outlet, and a steam inlet connectable to a chamber drain of the steam sterilizer, the steam inlet being connected to the ejector passage, and the ejector passage having a restriction for generating a vacuum at the steam inlet when water flows through the ejector passage from the ejector inlet to the ejector outlet;
    a reservoir for holding a quantity of water, the reservoir having a first reservoir outlet and a reservoir inlet;
    a pump, having a pump inlet and an outlet connected to the ejector inlet, for producing the flow of water through the ejector passage;
    a pump inlet conduit connecting the first reservoir outlet to the pump inlet;
    an ejector outlet conduit connecting the ejector outlet to the reservoir inlet;
    a second reservoir outlet;
    a drain conduit connectable from the second reservoir outlet to a drain;
    a water supply conduit connectable to a source of water;
    a first water supply passage connected from the water supply conduit directly to the pump inlet conduit, whereby water from the first water supply passage can be supplied from the water supply conduit to the pump without first passing through the reservoir;
    a first valve for controlling flow of water through the first water supply passage;
    a second water supply passage connected from said water supply conduit to the drain conduit for introducing water from the source of water into the drain conduit; and
    a second valve for controlling flow of water through the second water supply passage.

2. The vacuum unit according to claim 1, in which the reservoir inlet comprises a perforated tube having perforations, and connected to the ejector outlet conduit, for dispersing fluid drawn from the steam inlet into the reservoir.

3. The vacuum unit according to claim 1, in which the drain conduit includes a U-shaped trap.

4. The vacuum unit according to claim 3, in which the U-shaped trap comprises a first upright section connected to the second reservoir outlet, a second upright section having a drain outlet, and a connecting section connecting lower ends of the first and second upright sections, and in which the second water supply passage is connected, by a direct connection, to the second upright section.

5. The vacuum unit according to claim 4, including a temperature sensor located in the second upright section downstream from said direct connection, and in which the second valve is a sensor-responsive valve, connected, and responsive, to the temperature sensor.

6. The vacuum unit according to claim 1, in which the second water supply passage is connected, by a direct connection, to the drain conduit, including a temperature sensor located in the drain conduit, downstream from said direct connection, and in which the second valve is a sensor-responsive valve, connected and responsive, to the temperature sensor.

7. The vacuum unit according to claim 1, in which the reservoir has a top and a bottom, and in which the second reservoir outlet includes an upright tube located within the reservoir, the upright tube having an inlet opening adjacent the bottom of the reservoir, and an outlet connection adjacent the top of the reservoir.

8. The vacuum unit according to claim 7, in which the upright tube has an opening inside the reservoir adjacent the top of the reservoir.

9. The vacuum unit according to claim 1, in which:
the reservoir inlet comprises a perforated tube having perforations, and connected to the ejector outlet conduit, for dispersing fluid drawn from the steam inlet into the reservoir;
the drain conduit includes a U-shaped trap comprising a first upright section connected to the second reservoir outlet, a second upright section having a drain outlet, and a connecting section connecting lower ends of the first and second upright sections, and in which the second water supply passage is connected, by a direct connection, to the second upright section;
a temperature sensor is located in the second upright section downstream from said direct connection, and the second valve is a sensor-responsive valve, connected, and responsive, to the temperature sensor;
the reservoir has a top and a bottom;
the second reservoir outlet includes an upright tube located within the reservoir, the upright tube having an inlet opening adjacent the bottom of the reservoir, and an outlet connection adjacent the top of the reservoir; and
the upright tube has an opening inside the reservoir adjacent the top of the reservoir.

\* \* \* \* \*